United States Patent [19]

Williams et al.

[11] 4,178,386

[45] Dec. 11, 1979

[54] INHIBITORS OF GLYCOLIC ACID OXIDASE

[75] Inventors: Haydn W. R. Williams, Dollard des Ormeaux, Canada; Edward J. Cragoe, Jr., Lansdale; Clarence S. Rooney, Worcester, both of Pa.

[73] Assignee: Merck & Co., Inc., Rahway, N.J.

[21] Appl. No.: 950,754

[22] Filed: Oct. 11, 1978

[51] Int. Cl.² .............................................. A61K 31/19
[52] U.S. Cl. ..................................... 424/317; 424/314
[58] Field of Search ................................ 424/314, 317

[56] References Cited

PUBLICATIONS

Chemical Abstracts 77:149049v (1972).
Jewess et al., Febs Letters 53, p. 292 (1975).
Cromartie et al., J. Chem. Soc., Chem. Comm. 597 (1974).
Ghisla et al., Biochemistry, 15, p. 1791 (1976).
Verny et al., Bulletin de la Sociéte Chimique de France, 6, p. 2210 (1967).

*Primary Examiner*—Leonard Schenkman
*Attorney, Agent, or Firm*—Michael C. Sudol, Jr.; Harry E. Westlake, Jr.

[57] ABSTRACT

2-Hydroxy-3-butynoic acid is disclosed which inhibits glycolic acid oxidase and thus is useful in the treatment and prevention of calcium oxalate urolithiasis (calcium oxylate kidney and bladder stone disease).

2 Claims, No Drawings

INHIBITORS OF GLYCOLIC ACID OXIDASE

BACKGROUND OF INVENTION

Close to 70% of kidney stones are composed partially or predominantly of calcium oxalate. There is no satisfactory drug specific for the treatment of calcium oxalate urolithiasis, nor for prophylactic use by people prone to recurrent attacks of this disease.

A common treatment for urolithiasis due to calcium oxalate consists of surgical removal of stones, or control of the diet to restrict intake of calcium and/or oxalate, combined with ingestion of large quantities of water to dilute the urine. Attempts at chemotherapy have included the administration of magnesium oxide, orthophosphate, cellulose phosphate, isocarboxazide, thiazide diuretics, allopurinol and succinimide. Limited success had been realized by these drug approaches. No drug which specifically inhibits the biosynthetic formation of oxalic acid is available, or has been tested, for the treatment of calcium oxalate renal lithiasis.

The immediate metabolic precursor of the majority of the oxalate in the urine of a typical stone-former is glyoxylic acid. In turn its most important precursor is glycolic acid. The enzyme glycolate oxidase (GAO) is able to carry out the oxidation of glycolic acid, through glyoxylic acid to oxalic acid. Inhibition of this enzyme will therefore lead to a reduction in the concentration of oxalic acid in the kidney and bladder, reducing the probability that calcium oxalate crystallization will occur. Thus, inhibitors of glycolate oxidase provide a specific approach to the prevention and treatment of calcium oxalate urolithiasis.

SUMMARY OF THE INVENTION

It has been found that 2-hydroxy-3-butynoic acid when administered to animals reduces oxalic acid levels in the urine. This biological activity is useful in the prophylaxis and treatment of calcium oxalate urolithiasis, that is, this compound diminishes or prevents the formation of calcium oxylate kidney and bladder stones.

DETAILED DESCRIPTION

70% of all renal calculi contain oxalate as the main anionic component of the matrix. In many patients the condition is associated with a higher than average level of metabolically produced oxalate. The major pathway for biosynthesis of oxalate can be represented as follows:

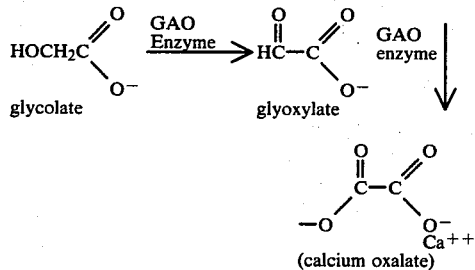

Glyoxylate is the major immediate precursor of oxalate. An inhibitor of glycolate oxidase will inhibit both the conversion of glyoxylate to oxalate, as well as the production of glyoxylate from glycolate. As a consequence of reducing oxalic acid levels in the urine with the compounds of this invention, the formation of oxalate calculi will be reduced or prevented.

2-Hydroxy-3-butynoic acid is a potent, irreversible inhibitor of glycolate oxidase which is effective in reducing oxalate levels in the urine of laboratory animals. It can therefore have application for the treatment and prevention of renal disease due to calcium oxalate stone formation in the kidney and bladder of humans. In the genetically inherited diseases termed hyperoxaluria types I and II, large quantities of oxalic acid are produced. Crystallization of calcium oxalate, occurring not only in the kidney and bladder, but in other tissues as well, frequently results in early death. The compounds of this invention could have major beneficial consequences for these patients.

2-Hydroxy-3-butynoic acid is a known compound and its preparation is shown in the following references:

T. Cromartie, J. Fisher, G. Kadzorowski, R. Lama, P. Marcotte, and C. Wash, J. C. S. Chem. Comm. 597 (1974). P. J. Jewess, M. W. Kerr, and D. P. Whitaker, FEBS Lett. 53, 292 (1975).

A detailed procedure is shown under Example 1.

Included within the scope of the invention are the pharmaceutically acceptable salts and lower alkyl ($C_{1-6}$) esters of 2-hydroxy-3-butynoic acid. 2-Hydroxy-3-butynoic acid is a typical organic acid with a pKa in the range of 4. Thus salts are readily formed with the usual inorganic cations such as sodium, potassium and ammonium, or tetraalkyl ammonium. Salts with organic amines such as trimethylamine, triethylamine, n-butylamine and the like are also suitable. The neutralization can be carried out by a variety of procedures known to the art to be generally useful for the preparation of such salts. The choice of the most suitable procedure will depend on a variety of factors including convenience of operation, economic considerations, and particularly the solubility characteristics of the particular free base, the acid, such as the methyl to hexyl esters and the acid addition salt. Lower alkyl esters can be prepared by known procedures (See M. Verny and R. Vessiere, Bull. Soc. Chim. Fr., 2210-16 (1967)).

The 2-hydroxy-3-butynoic acid or pharmaceutically acceptable salts and lower alkyl esters, can be administered to patients (both human and animal) having, or being prone to, calcium oxalate urolithiasis by formulating them in composition such as tablet, capsule or elixir for oral administration. Sterile solutions or suspensions can be used for parenteral administration. About 10 to 500 mg of 2-hydroxy-3butynoic acid or a pharmaceutically acceptable salt is compounded with a pharmaceutically acceptable vehicle, carrier, excipient, binder, preservative, stabilizer, flavor, etc., in a unit dosage form as called for by accepted pharmaceutical practice. The amount of acitve substance in the composition is such that dosage in the range indicated is obtained. The total daily dose administered to a patient having or being prone to calcium oxalate kidney or bladder stone disease will be in the 20 mg to 2000 mg range, with a preferred daily dose being 50 mg to 1000 mg of active ingredient. It will be realized by those skilled in the art that the dosage range for any particular patient (animal or human) will depend upon the severity of the disease treated, weight of the patient and any other condition which the physician or other person skilled in the art will take account of.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a seeetening agent such as sucrose, lactose, or saccharin; a flavoring agent such as peppermint, oil of wintergreen or cherry. When the dosage unit form is a capsule, it may contain in addition to materials of the above type, a liquid carrier such as a fatty oil. Various other materials may be present as coatings to otherwise enhance the pharmaceutical elegance of the preparation. For instance, tablets may be coated with shellac, sugar or the like. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples, given by way of illustration and not to be construed as limiting, further clarify the invention.

EXAMPLE 1

Preparation of 2-Hydroxy-3-butynoic Acid

To a slurry of sodium cyanide (57 g, 1.16 mole) in diethyl ether (800 ml) is added initially acetic acid (3 ml). This is followed immediately by the simultaneous dropwise addition of acetic acid (total quantity 70 g, 1.16 mole) and a solution of propargyl aldehyde (39.9 g, .74 mole) in ether (50 ml). The complete mixture, after additions, is stirred for 5 hours. After filtration, drying with $Na_2SO_4$, and evaporation, a brown oil (33.2 g) is obtained (cyanhydrin intermediate).

To the cyanhydrin intermediate (28.7 g, 0.35 mole) concentrated HCl (50 ml) is added slowly, with stirring and cooling to maintain the temperature in the 25°–30° C. range. After addition is complete, the mixture is heated to 50° for 0.75 hours. After cooling and addition of $H_2O$ (50 ml) the solution is extracted with ether (8×150 ml) to give crude 2-hydroxy-3-butynoic acid (32.2 g) as a brown oil. This product is added to conc. $NH_4OH$ (100 ml) cooled to an ice bath. The brown solution is evaporated, ethanol (100 ml) added, and the solution re-evaporated. To the solid residue is added ethanol (100 ml). Filtration gives tan-colored 2-hydroxy-3-butynoic acid ammonium salt (27.1 g, m.p. 124°–125° C.). Purification is accomplished by dissolving the solid in a mixture of $H_2O$ (50 ml) and conc. $NH_4OH$ (5 ml), filtering through charcoal to decolorize, and evaporation. The solid residue is slurried with ethanol (100 ml) and filtered to give pure 2-hydroxy-3-butynoic acid ammonium salt (22.5 g, m.p. 128°–129° C.).

EXAMPLE 2

Dry-filled capsules containing 50 mg of active ingredient per capsule

|  | Per Capsule |
| --- | --- |
| 2-Hydroxy-3-butynoic acid ammonium salt | 50 mg. |
| Lactose | 149 mg. |
| Magnesium Stearate | 1 mg. |
| Capsule (Size No. 1) | 200 mg. |

The 2-hydroxy-3-butynoic acid salt is reduced to a No. 60 powder and then lactose and magnesium stearate are passed through a No. 60 bolting cloth onto the powder and the combined ingredients admixed for 10 minutes and then filled into a No. 1 dry gelatin capsule.

What is claimed is:

1. A method of treating or preventing the formation of calcium oxalate kidney or bladder stones which comprises administering to a patient with or prone to this disease an effective amount of 2-hydroxy-3-butynoic acid or a pharmaceutically acceptable salt or lower alkyl ester thereof.

2. A method of claim 1 wherein the compound administered is 2-hydroxy-3-butynoic acid.

* * * * *